(12) United States Patent
Chojin

(10) Patent No.: US 8,382,792 B2
(45) Date of Patent: *Feb. 26, 2013

(54) END EFFECTOR ASSEMBLY FOR ELECTROSURGICAL DEVICE

(75) Inventor: Edward M. Chojin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 622 days.

This patent is subject to a terminal disclaimer.

(21) Appl. No.: 12/361,367

(22) Filed: Jan. 28, 2009

(65) Prior Publication Data

US 2009/0209960 A1  Aug. 20, 2009

Related U.S. Application Data

(60) Provisional application No. 61/028,687, filed on Feb. 14, 2008.

(51) Int. Cl.
*A61B 17/00* (2006.01)
(52) U.S. Cl. ........................................ 606/206
(58) Field of Classification Search .......... 606/51, 606/52, 205–209
See application file for complete search history.

(56) References Cited

U.S. PATENT DOCUMENTS

| | | | |
|---|---|---|---|
| 5,052,402 A * | 10/1991 | Bencini et al. ............... 600/564 |
| 5,527,313 A | 6/1996 | Scott et al. | |
| 5,611,808 A | 3/1997 | Hossain et al. | |
| 6,113,598 A | 9/2000 | Baker | |
| 6,126,658 A | 10/2000 | Baker | |
| 6,443,970 B1 | 9/2002 | Schulze et al. | |
| 6,458,128 B1 | 10/2002 | Schulze | |
| 6,464,702 B2 | 10/2002 | Schulze et al. | |
| 6,620,161 B2 | 9/2003 | Schulze et al. | |
| 6,652,521 B2 | 11/2003 | Schulze | |
| 6,695,840 B2 | 2/2004 | Schulze | |
| 6,790,217 B2 | 9/2004 | Schulze et al. | |
| 7,377,920 B2 * | 5/2008 | Buysse et al. ............... 606/50 |
| 2002/0099372 A1 | 7/2002 | Schulze et al. | |
| 2004/0236326 A1 | 11/2004 | Schulze et al. | |
| 2010/0094287 A1 * | 4/2010 | Cunningham et al. ........ 606/51 |
| 2010/0179547 A1 * | 7/2010 | Cunningham et al. ........ 606/51 |

FOREIGN PATENT DOCUMENTS

| | | |
|---|---|---|
| CA | 2104423 | 2/1994 |
| DE | 2415263 | 10/1975 |
| DE | 2514501 | 10/1976 |
| DE | 2627679 | 1/1977 |
| DE | 3612646 | 4/1987 |

(Continued)

OTHER PUBLICATIONS

U.S. Appl. No. 12/336,970, filed Dec. 17, 2008.

(Continued)

*Primary Examiner* — Nicholas Lucchesi
*Assistant Examiner* — Pritesh Patel

(57) ABSTRACT

A bipolar forceps is provided and includes a housing having a shaft that extends therefrom which defines a longitudinal axis therethrough. The housing including a drive assembly disposed therein and is operable to reciprocate an actuation tube within the shaft. The bipolar forceps includes an end effector assembly operatively connected to a distal end of the shaft and has a pair of first and second jaw members. The first and second jaw members are pivotable about a living hinge and are adapted to connect to an electrosurgical energy source. Each of the jaw members includes a cam slot defined at a proximal end thereof. One or more of the jaw members is operatively connected to a distal end the actuation tube via a cam pin such that distal reciprocation of the actuation tube cams each of the jaw members towards one another about the respective living hinge to grasp tissue.

18 Claims, 9 Drawing Sheets

FOREIGN PATENT DOCUMENTS

| | | |
|---|---|---|
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0589453 | 3/1994 |
| EP | 1159926 | 12/2001 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO99/40861 | 8/1999 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument" ; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.

Craig Johnson, "Use of the LigaSure Vessel Sealing System in Bloodless Hemorrhoidectomy" Innovations That Work, Mar. 2000.

Levy et al. "Use of a New Energy-based Vessel Ligation Device During Vaginal Hysterectomy" Int'l Federation of Gynecology and Obstetrics (FIGO) World Congress 1999.

Barbara Levy, "Use of a New Vessel Ligation Device During Vaginal Hysterectomy" FIGO 2000, Washington, D.C.

E. David Crawford "Use of a Novel Vessel Sealing Technology in Management of the Dorsal Venous Complex" Sales/Product Literature 2000.

Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.

McLellan et al. "Vessel Sealing for Hemostasis During Pelvic Surgery" Int'l Federation of Gynecology and Obstetrics FIGO World Congress 2000, Washington, D.C.

McLellan et al. "Vessel Sealing for Hemostasis During Gynecologic Surgery" Sales/Product Literature 1999.

Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

END EFFECTOR ASSEMBLY FOR ELECTROSURGICAL DEVICE

CROSS-REFERENCE TO RELATED APPLICATIONS

This application claims the benefit of priority to U.S. Provisional Application Ser. No. 61/028,687 entitled "END EFFECTOR ASSEMBLY FOR ELECTROSURGICAL DEVICES" filed Feb. 14, 2008 by Edward Chojin, which is incorporated by reference herein.

BACKGROUND

1. Technical Field

The present disclosure relates to an electrosurgical forceps and, more particularly, the present disclosure relates to electrosurgical forceps, which employ a flexible end effector assembly for use with either an endoscopic or open electrosurgical forceps.

2. Description of Related Art

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from three millimeters to twelve millimeters. Smaller cannulas are usually preferred, which, as can be appreciated, ultimately presents a design challenge to instrument manufacturers who must find ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

As is known in the art, bipolar forceps typically employ end effector assemblies that include one or more jaw members. Commonly, end effector assemblies include intricate pivot mechanisms that may employ one or more moving components, which are machined together. Pivot mechanisms assembled in such a manner may prove to be more costly to manufacture and more likely to fail. Because there are more components, there is an increased likelihood that one or more of those moving components may fail, which, in turn, may compromise the integrity and/or performance of the pivot mechanism.

SUMMARY

It is one aspect of the present disclosure to provide a bipolar forceps that includes a housing having a shaft that extends therefrom which defines a longitudinal axis therethrough. The housing includes a drive assembly disposed therein; the drive assembly is operable to reciprocate an actuation tube within the shaft. The drive assembly includes an actuation rod which operably couples to the actuation tube to actuate the jaw members. The bipolar forceps also includes an end effector assembly operatively connected to a distal end of the shaft having a pair of first and second jaw members. Each of the first and second jaw members is pivotable about a living hinge and being adapted to connect to an electrosurgical energy source. Each of the jaw members including a cam slot defined at a proximal end thereof. The cam slot of one or more of the jaw members is over molded on the at least one jaw member that is connected to the actuation tube. The cam slot may have a generally concave or arcuate structure.

In an embodiment, the jaw members are operatively connected to a distal end the actuation tube via a cam pin such that distal reciprocation of the actuation tube cams each of the jaw members towards one another about the respective living hinge to grasp tissue or seal.

The jaw members are electrically isolated from each other via a non-conductive spacer disposed at a proximal end therebetween, the spacer providing a gap distance from about 0.001 inches to 0.006 inches between jaw members when closed. In embodiments the gap distance may be less than 0.001 inches or greater than 0.006 inches.

In an embodiment, each jaw member includes an outer insulative housing which is overmolded or coated to capture a sealing plate for engaging tissue, the outer insulative housing being configured to include the cam slot at a proximal end thereof. Other embodiments may include the jaw member having an insulative housing and a sealing plate that are integrally formed together.

It is another aspect of the present disclosure to provide a bipolar forceps that includes a housing having a shaft which extends therefrom, which defines a longitudinal axis therethrough, the shaft including cam pins located at a distal end thereof and at least one groove. The housing includes a drive assembly disposed therein; the drive assembly being operable to reciprocate an actuation tube within the shaft. The bipolar forceps also includes an end effector assembly operatively connected to a distal end of the shaft having a pair of first and second jaw members. Each of the first and second jaw members is pivotable about a living hinge and being adapted to connect to an electrosurgical energy source. Each of the jaw members includes a cam slot defined at a proximal end thereof and at least one support member operatively connected to the at least one groove.

It is yet another aspect of the present disclosure to provide a bipolar forceps that includes a housing having a shaft which extends therefrom which defines a longitudinal axis therethrough. The shaft including cam pins located at a distal end thereof. The housing includes a drive assembly disposed therein. The drive assembly is operable to reciprocate an actuation rod within the shaft. The bipolar forceps also includes an end effector assembly operatively connected to a distal end of the shaft having a pair of first and second jaw members. Each of the first and second jaw members is pivotable about a living hinge and is adapted to connect to an electrosurgical energy source. Each of the jaw members includes a cam slot defined at a proximal end thereof and operatively connected to the cam pins of shaft.

The present disclosure also provides a method for performing an electrosurgical procedure. The method includes the steps of providing a bipolar forceps. The bipolar forceps includes housing. The housing having a shaft that extends therefrom that defines a longitudinal axis therethrough. Disposed within he housing is a drive assembly being operable to reciprocate an actuation tube within the shaft to actuate a pair of first and second jaw members about a living hinge. Additionally, each of the jaw members includes a cam slot defined at a proximal end thereof. One or more of the jaw members is operatively connected to a distal end the actuation tube via a cam pin. The method also includes the steps of positioning tissue between the pair of first and second jaw members; actuating the drive assembly to move the actuation tube, which causes the cam pin to cam the first and second jaw members to pivot about the living hinge and cam towards each other such that tissue is grasped therebetween; and applying electrosurgical energy to the jaw members such that a tissue seal may be effected therebetween.

DETAILED DESCRIPTION

Detailed embodiments of the present disclosure are disclosed herein; however, the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

As mentioned above, electrosurgical forceps typically include intricate and sometimes expensive end effector assemblies having one or more jaw members. The electrosurgical forceps of the present disclosure employs a shaft operatively connected to an end effector assembly that includes an actuation tube movable from a first position to second position and a pair of opposing jaw members. The actuation tube is operatively connected to one or more jaw members for moving the jaw members from an open configuration in a spaced relation relative to one another to a closed configuration for effecting a tissue seal therebetween. The jaw members may be bent, in an open configuration, at a living hinge located at a proximal end thereof.

Figure 1:
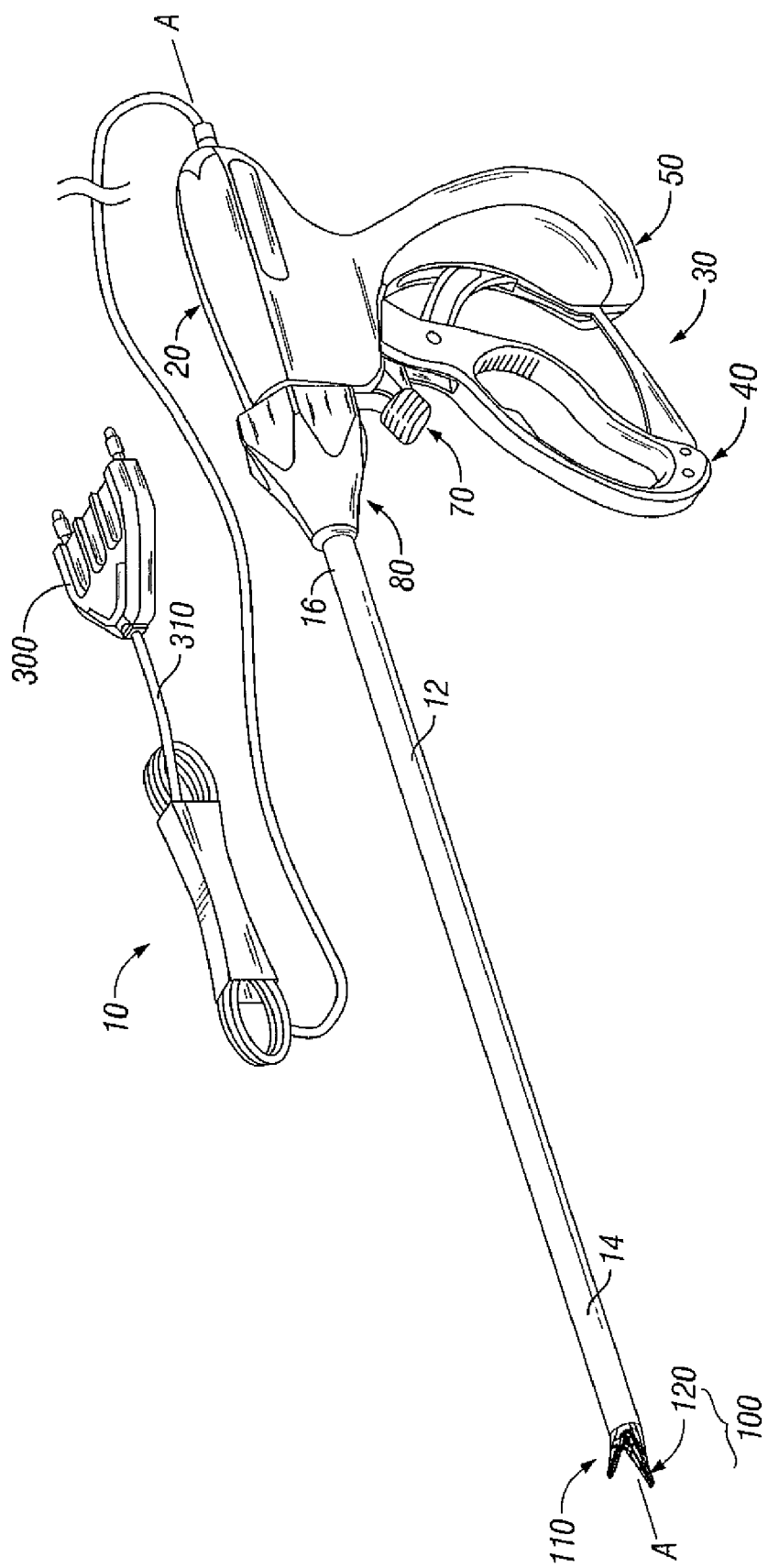
FIG. 1 is a perspective view of a bipolar forceps in accordance with the present disclosure.
Figure 2:
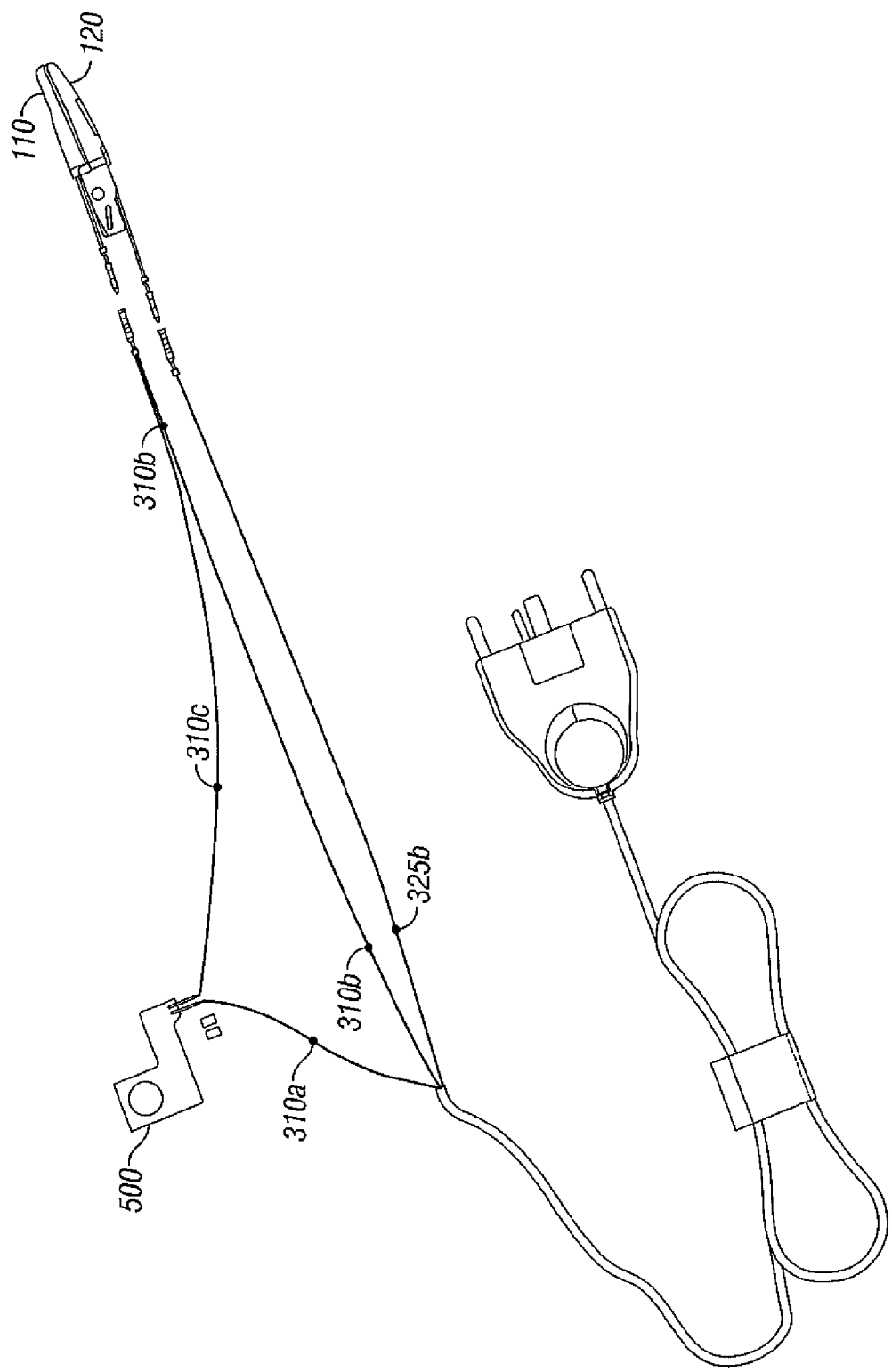
FIG. 2 is a schematic diagram of the electrical configuration of the bipolar forceps in accordance with the present disclosure.

Turning now to FIG. 1 one embodiment of an electrosurgical forceps 10 is shown. For the remainder of the disclosure it will be assumed that the electrosurgical forceps is a bipolar forceps; keeping in mind that any electrosurgical forceps may be employed with the present disclosure. Bipolar forceps 10 is shown for use with various electrosurgical procedures and generally includes a housing 20, a handle assembly 30, a rotating assembly 80, a trigger assembly 70, a drive assembly 130, and an end effector assembly 100, which operatively connects to the drive assembly 130 via an actuation tube 200 (see FIGS. 3-4C). End effector assembly 100 includes opposing jaw members 110 and 120, which mutually cooperate to grasp, seal and, in some cases, divide large tubular vessels and large vascular tissues. Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument; however, an open version of the forceps may also include the same or similar operating components and features as described below.

Forceps 10 includes a shaft 12, to be described in greater detail below, which has a distal end 14 configured in such a manner that a drive rod 132 of drive assembly 130 mechanically engages the end effector assembly 100 and a proximal end 16 which mechanically engages the housing 20. In the drawings and in the descriptions that follow, the term "proximal," as is traditional, will refer to the end of the forceps 10 which is closer to the user, while the term "distal" will refer to the end which is farther from the user.

With continued reference to FIG. 1, handle assembly 30 includes a fixed handle 50 and a movable handle 40. Fixed handle 50 is integrally associated with housing 20 and handle 40 is movable relative to fixed handle 50. Fixed handle 50 may include one or more ergonomic enhancing elements to facilitate handling, e.g., scallops, protuberances, elastomeric material, etc.

Movable handle 40 of handle assembly 30 is ultimately connected to drive assembly 130 including drive rod 132, which together mechanically cooperate to impart movement of actuation tube 200. Movement of actuation tube 200 causes jaw members 110 and 120 to move from an open position, wherein the jaw members 110 and 120 are disposed in spaced relation relative to one another, to a clamping or closed position, wherein the jaw members 110 and 120 cooperate to grasp tissue therebetween.

Rotating assembly 80 is operatively associated with the housing 20 and is rotatable approximately 180 degrees about a longitudinal axis "A-A" defined through shaft 12 (see FIG. 1).

Forceps 10 also includes an electrosurgical cable 310 that connects the forceps 10 to a source of electrosurgical energy, e.g., a generator 500 (shown schematically). It is contemplated that generators such as those sold by Valleylab—a division of Tyco Healthcare Group LP, located in Boulder Colorado may be used as a source of electrosurgical energy, e.g., Ligasure™ Generator, FORCE EZ™ Electrosurgical Generator, FORCE FX™ Electrosurgical Generator, FORCE 1C™, FORCE 2™ Generator, SurgiStat™ II or other envisioned generators that may perform different or enhanced functions.

Cable 310 is internally divided into cable leads 310a, 310b and 325b which are designed to transmit electrical potentials through their respective feed paths through the forceps 10 to the end effector assembly 100. More particularly, cable feed 325b connects through the forceps housing 20 and through the rotating assembly to jaw member 120. Lead 310a connects to one side of a switch (not shown) and lead 310c connects to the opposite side of the -switch such that upon activation of the switch energy is transmitted from lead 310a to 310c. Lead 310c is spliced with lead 310b which connects through the rotating assembly to jaw member 110.

For a more detailed description of handle assembly 30, movable handle 40, rotating assembly 80, electrosurgical cable 310 (including line-feed configurations and/or connections), and drive assembly 130 reference is made to commonly owned patent application Ser. No., 10/369,894, filed on Feb. 20, 2003, entitled VESSEL SEALER AND DIVIDER AND METHOD OF MANUFACTURING THE SAME.

Figure 3:
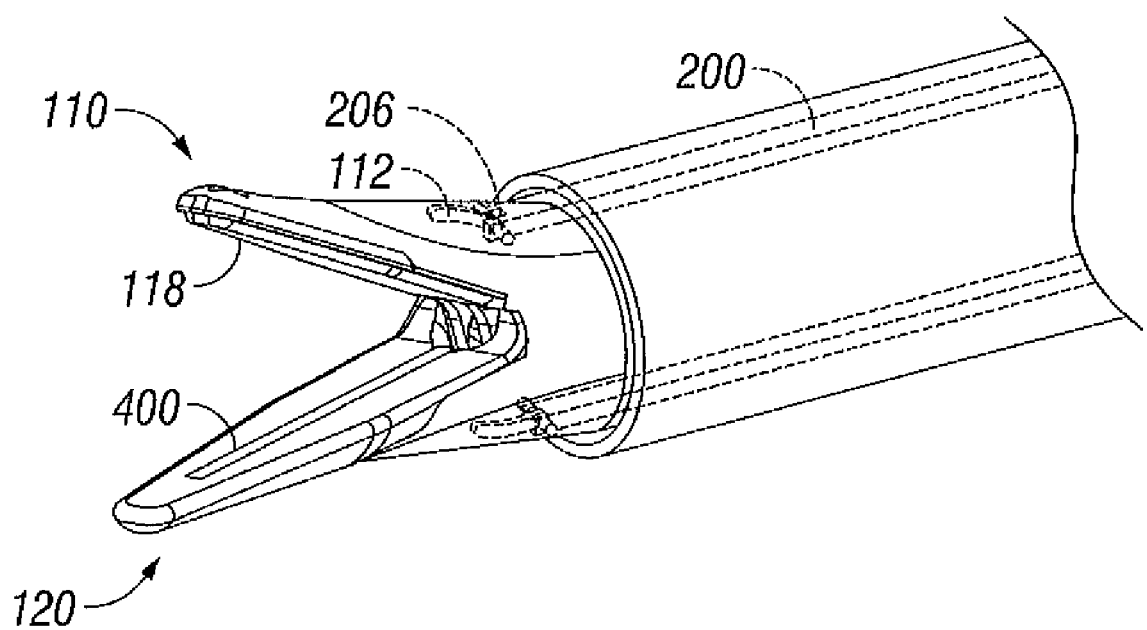
FIG. 3 is a perspective view of an end effector assembly according to an embodiment in accordance with the present disclosure.
Figure 4A:
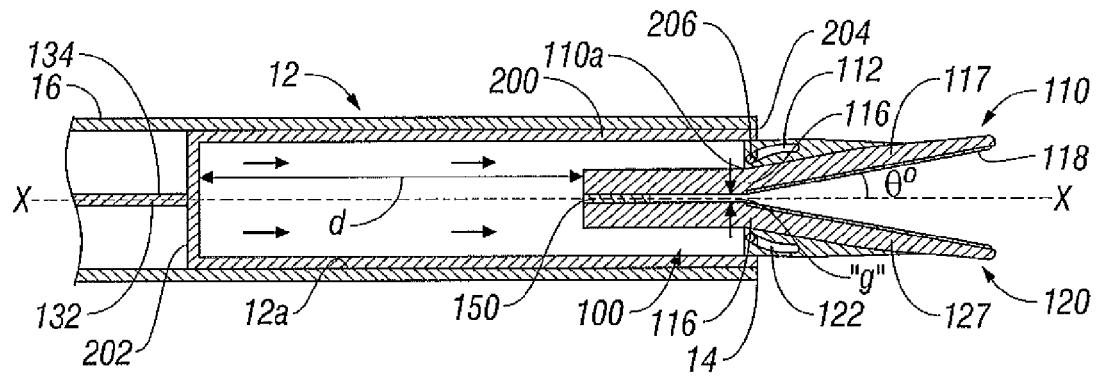
FIGS. 4A-4C illustrates the end effector assembly depicted in FIG. 3 in open, intermediate and closed configurations.
Figure 4B:
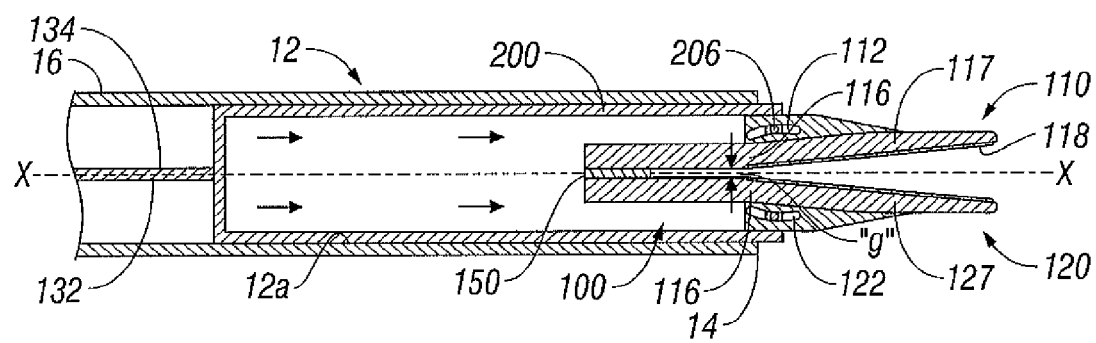
Figure 4C:
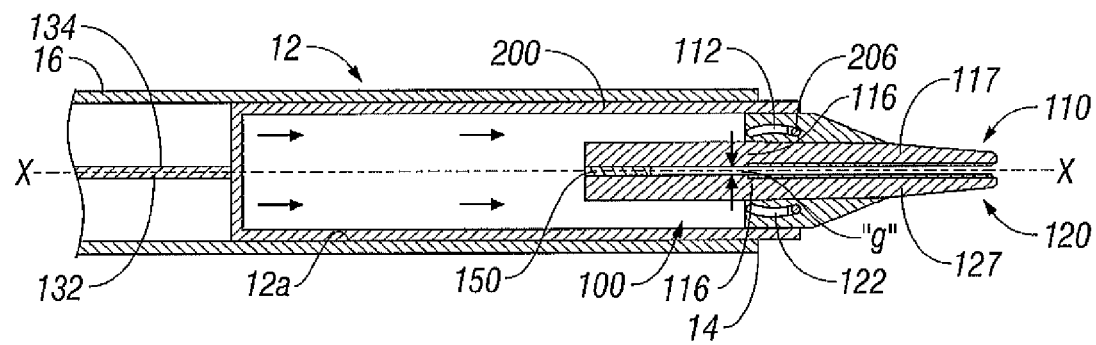

Turning now to FIGS. 3-4C, shaft 12 includes proximal end 16 operatively connected to handle 30, and distal end 14 operatively connected to end effector assembly 100 and actuation tube 200. Shaft 12 is configured to house drive assembly 130 and actuation tube 200 or portions thereof. At distal end 14 of shaft 12, jaw members 110 and 120, or portions thereof, are attached to an inner surface 12a of shaft 12 via any suitable attaching means known in the art including but not limited to staking, welding, riveting, molding or overmolding.

Distal end 14 of shaft 12 is adapted to reciprocate actuation tube 200. Additionally, distal end 14 is dimensioned to allow jaw members 110 and 120 to flex, from an opened to closed configuration, during translation of actuation tube 200.

With continued reference to FIGS. 3-4C, actuation tube 200 is shown. Actuation tube 200 may be manufactured from any suitable material including but not limited to plastic, metal, and the like. Actuation tube 200 may have any suitable geometric shape. In the illustrated embodiment, actuation tube 200 includes a proximal end 202 and distal end 204 defining a generally cylindrical structure, which includes one or more cam pins 206. Actuation tube 200 is configured for longitudinal translation with respect to each of jaw members 110 and 120, and spacer 150.

Actuation tube 200 is configured to fit within shaft 12, such that when drive rod 132 of drive assembly 130 is translated in a distal direction, cam pins 206 of actuation tube 200 ride along a corresponding number of cam slots 112 and 122 located on the jaw members 110 and 120, respectively (two cam pins are shown in the drawings).

More particularly, proximal end 202 of actuation tube 200 is operatively connected to distal end 134 of drive rod 132, set back approximately a distance "d" from a proximal end of jaw members 110 and 120. A distal end 204 of actuation tube 200 is operatively connected to, and in mechanical communication with, one or more of the jaw members 110, 120 (both jaw members 110 and 120 are shown in mechanical communication with distal end 204). The distances that proximal end 202 of actuation tube 200 and distal end 134 of drive rod 132 may be set back from the proximal end of spacer 150 may vary. For example, distance "d" may be a distance that allows actuation tube 200 to translate distally and cause jaw members 110 and 120 to go from an open configuration to a closed configuration, as shown in FIGS. 4A-4C.

Distal end 204, or a portion thereof, of actuation tube 200 is configured for translation within shaft 12. Distal end 204 is operatively connected to one or more of cam slots 112 and 122 of jaw members 110 and 120, respectively, via mechanical engagement between one or more cam pins 206 (two cam pins 206 are shown).

Cam pins 206 extend laterally from an inside surface of actuation tube 200 and are configured to mechanically communicate with cam slots 112 and 122 to move the jaw members 110 and 120 from the open (FIG. 4A) to closed (FIG. 4C) configurations. Because jaw members 110 and 120 are in electrical communication with a source of electrosurgical energy, it may be useful to have cam pin 206, or portion thereof, manufactured from a non-conductive material. Cam pin 206 may be biased in a direction that is normal to the longitudinal axis "X". Having a cam pin 206 biased in such a manner may facilitate closing the jaw members 110, 120.

End effector assembly 100 includes opposing jaw members 110 and 120 that are fixedly attached to inner surface 12a of shaft 12. Located between jaw members 110 and 120 may be a non-conductive spacer 150 configured to set a rear gap distance therebetween, to be described in more detail below. Jaw members 110 and 120 are generally symmetrical and include similar component features which cooperate to effect the sealing and dividing of tissue. As a result, and unless otherwise noted, only jaw member 110 and the operative features associated therewith are described in detail herein, but as can be appreciated many of these features, if not all, apply to equally jaw member 120 as well.

Jaw member 110 includes an insulative jaw housing 117 and an electrically conductive seal plate 118 (hereinafter seal plate 118). The insulator 117 is configured to securely engage the electrically conductive seal plate 118. Seal plate 118 may be manufactured from stamped steel. This may be accomplished by stamping, by overmolding, by overmolding a stamped electrically conductive sealing plate and/or by overmolding a metal injection molded seal plate. All of these manufacturing techniques produce an electrode having a seal plate 118 that is substantially surrounded by the insulating substrate. Within the purview of the present disclosure, jaw member 110 may include a jaw housing 117 that is integrally formed with a seal plate 118.

Jaw member 120 includes a similar structure having an outer insulative housing 127 that is overmolded (to capture seal plate 128).

Jaw member 110 includes a living hinge located at a proximal end 11a thereof. Proximal end 110a of jaw member 110 is bent near a distal end of spacer 150, such that a living hinge 116 is formed. Hinge 116 is bent in such a manner that an angle θ is formed relative to the longitudinal axis "X", as best seen in FIG. 3 and 4A. The angle θ may be between 0° and 90°. Other angles θ of the jaw member 110 relative to the longitudinal axis "X" are contemplated and within the scope of the present disclosure.

Cam slot 112 is located on a surface of jaw member 110 and interacts with cam pin 206 of actuation tube 200, as shown in FIGS. 4A-4C. Cam slot 112 may be formed on jaw member 110 by any of the previously described stamping and/or overmolding manufacturing techniques and may be formed by other suitable methods, e.g., drilling, etching, or machining, and so on. Cam slot 112 is configured in a manner such that when cam pin 206 rides along cam slot 112 jaw member 110 pivots about living hinge 116. While cam slot 112 is depicted as having a generally concave or arcuate structure, cam slot 112 may have any suitable structure that will allow jaw member 110 to function as described above. Cam slot 112 may be formed on a side surface (not explicitly shown), of jaw member 110. This, of course, will depend on the contemplated uses by the manufacturer.

Cam slot 122, operatively formed on jaw member 120, is configured in a manner that is the same as or substantially similar to cam slot 112 of jaw member 110.

Spacer 150 may be integrally formed with one or both of the jaw members 110 and 120, via any of the previously described manufacturing techniques, e.g., stamping and/or overmolding. Alternatively, spacer 150 may be a separate member operatively connected to each of the jaw members 110 and 120, or operatively connected to a distal end 14 of shaft 12. As mentioned above, spacer 150 may be configured to define a gap distance "g" between jaw members 110 and 120 (FIGS. 4A-4C). Gap distance may be any suitable distance; however, in one embodiment, gap distance "g" may be between about 0.001 inches and 0.006 inches. Gap distances less than 0.001 inches and greater than 0.006 inches are within the purview of the present disclosure. Spacer 150 is configured to isolate the electrically conductive seal surfaces 118 and 114 of jaw members 110 and 120, respectively. Spacer 150 may be formed from any suitable material including but not limited plastics, metals, and the like. Spacer 150 may be either conductive, non-conductive, or a combination thereof.

Spacer 150 may include a knife slot (not explicitly shown) defined therethrough configured to receive a knife blade, or portion thereof, and allow translation of the knife blade therethrough. The knife slot may extend distally from spacer 150 and substantially align with a knife slot 400 located on one or more of the jaw members 110 and 120 (FIG. 3)

In use, prior to sealing tissue, jaw members 110 and 120 may initially be biased in an open configuration, each disposed at an angle θ relative to the longitudinal axis "X", and actuation tube 200 may be set back at a distance "d" from the proximal end of jaw member (FIG. 4A). When tissue is ready to be grasped for treating, a user positions tissue between jaw members 110 and 120, and squeezes handle 40 which, in turn, causes drive rod 132 of drive assembly 103 to translate distally. As drive rod 132 is translated distally, actuation tube 200 translates distally, which, in turn, causes cam pins 206 to ride along cam slots 112 and 122 of jaw members 110 and 120, respectively. As actuation tube 200 moves distally, jaw members 110 and 120 will flex radially inwardly, about living hinge 116, toward each other and the longitudinal axis "X" (FIG. 4B). When proximal end 202 of actuation tube 200 has moved approximately a distance "d", jaw members 110 and 120 will be substantially parallel to each other and the longitudinal axis "X", separated approximately by a gap distance "g" causing tissue to be grasped therebetween (FIG. 4C). After tissue is grasped between jaw members 110 and 120, electrosurgical energy may be transmitted to the jaw members 110 and 120 effecting a tissue seal therebetween, or other suitable tissue effect.

Upon completion of effecting a tissue seal, a user releases handle 40, which, in turn, causes drive rod 132 of drive rod assembly 130 to translate proximally. As drive rod 132 is translated proximally, actuation tube 200 translates proximally, which, in turn, causes cam pins 206 to ride along cam slots 112 and 122 of jaw members 110 and 120, respectively. As actuation tube 200 moves proximally, jaw members 110 and 120 will flex radially outward, about living hinge 116, away from each other and the longitudinal axis "X" (FIG. 4B). When proximal end 202 of actuation tube 200 has moved approximately a distance "d", jaw members 110 and 120, returning to their initial open configuration, will again be disposed at an angle θ relative to the longitudinal axis "X" (FIG. 4A).

Figure 5:
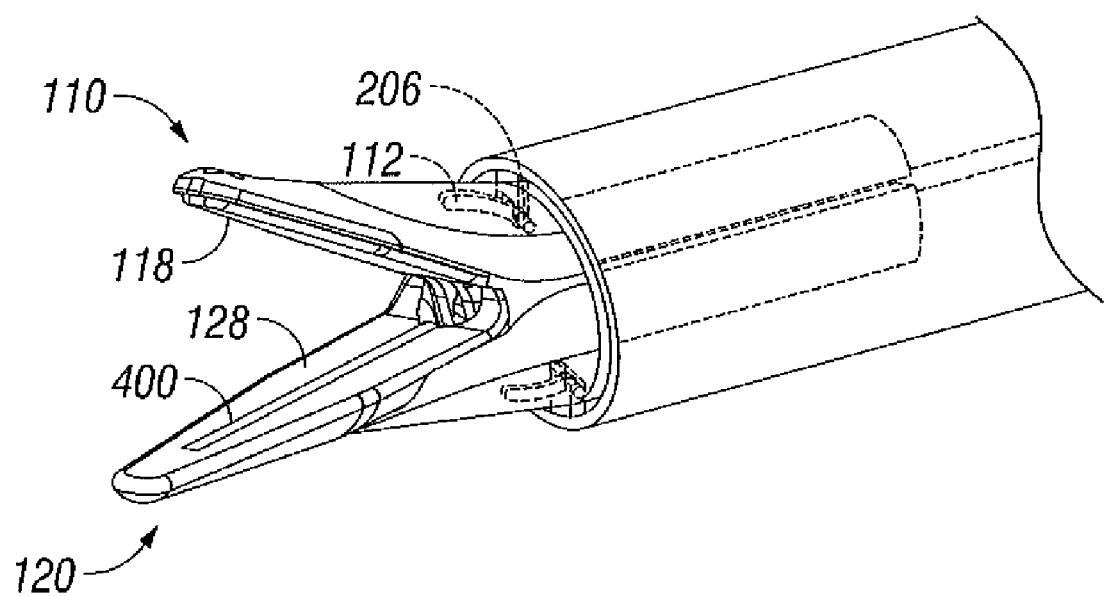
FIG. 5 is perspective view of an end effector assembly according to another embodiment in accordance with the present disclosure.
Figure 6A:
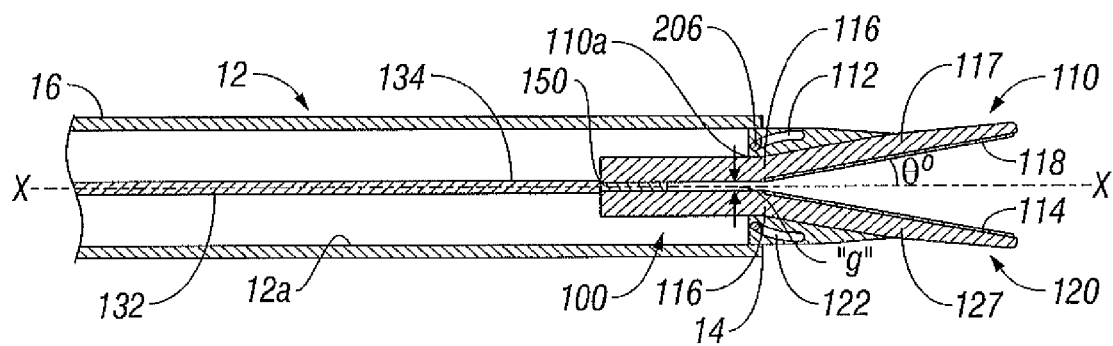
FIGS. 6A-6C illustrates the end effector assembly depicted in FIG. 5 in open, intermediate and closed configurations.
Figure 6B:
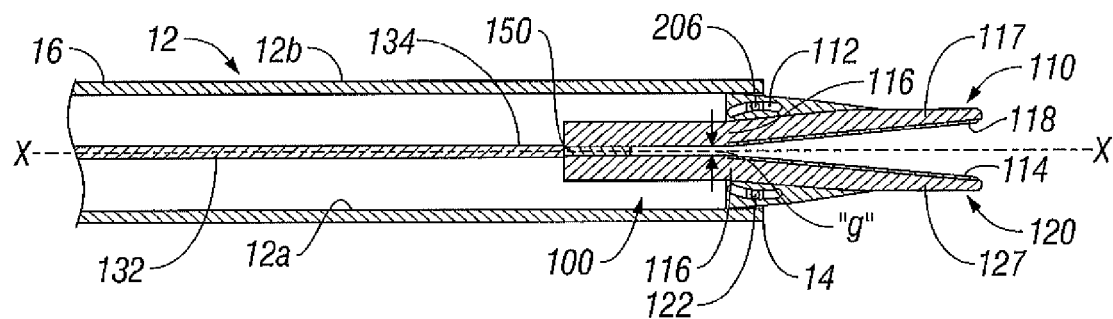
Figure 6C:
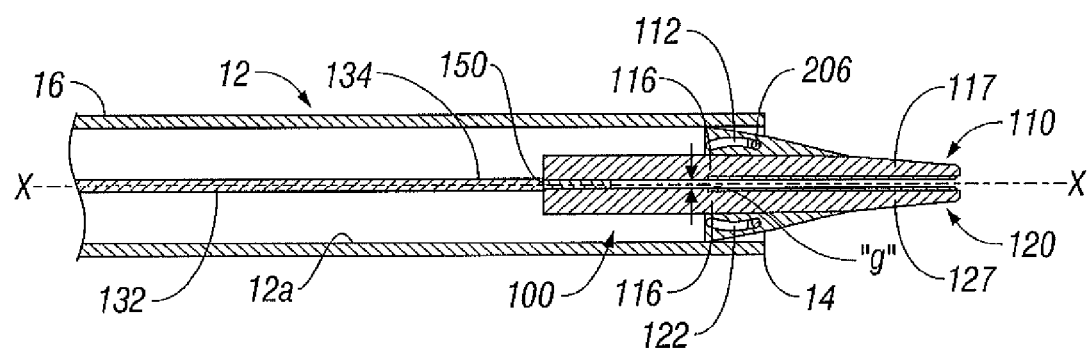

Turning now to FIGS. 5-6C, in which like numerals indicate like parts, a bipolar forceps 300 is shown. Bipolar forceps 300 is substantially similar to the bipolar forceps 10 described hereinabove and thus will only be described herein to the extent necessary to identify differences in construction and/or operation thereof.

Bipolar forceps 300 includes a shaft 12 having inner and outer surfaces, 12a and 12b, respectively, and operatively connected to jaw members 110 and 120 of end effector assembly 100. At distal end 14 of shaft 12, extending laterally from inner surface 12a, are one or more cam pins 206 (two cam pins are shown) operatively connected thereto, and in mechanical communication with one or more cam slots 112 and 122 located on jaw members 110 and 120, respectively. Cam pins 206 may be configured in a manner as described above.

Drive assembly 130 includes a drive rod 132 having a distal end operatively connected to a proximal end of the jaw members. Drive rod 132 is configured for providing translatable movement of the jaw members.

Spacer 150 may be configured in a manner the same as or substantially similar as described hereinabove. Jaw members 110 and 120 also may be configured in a manner as described above. Thus, for the purposes of brevity only those operative features unique to jaw members 110 and 120 will be discussed hereinafter.

Jaw members 110 and 120 include cam slots 112 and 122, respectively, operatively connected to cam pins 206 of shaft 12. Jaw members 110 and 120, or portion thereof may be integrally formed with spacer 150.

In use, prior to sealing tissue, jaw members 110 and 120 may be initially in an open configuration, each disposed at an angle θ relative to the longitudinal axis "X" (FIG. 6A). When tissue is ready to be sealed, a user positions tissue between jaw members 110 and 120 and squeezes handle 40 causing drive rod 132 of drive rod assembly 130 to translate proximally. As drive rod 132 translates proximally, jaw members 110 and 120 will also translate proximally, which, in turn, causes cam pins 206 to ride along cam slots 112 and 122 of jaw members 110 and 120, respectively. As jaw members 110 and 120 move proximally, jaw members 110 and 120 will flex radially inwardly, about living hinge 116, toward each other and the longitudinal axis "X" (FIG. 6B). When jaw members 110 and 120 are in their proximal most position, jaw members 110 and 120 will be substantially parallel to each other and the longitudinal axis "X", separated approximately by a gap distance "g" causing tissue to be grasped therebetween (FIG. 6C). After tissue is grasped between jaw members 110 and 120, electrosurgical energy may be transmitted to the jaw members 110 and 120 effecting a tissue seal therebetween, or other suitable tissue effect.

Upon completion of effecting a tissue seal, a user releases handle 40, causing drive rod 132 of drive rod assembly 130 to translate distally. As drive rod 132 translates distally, jaw members 110 and 120 will also translate distally, which, in turn, causes cam pins 206 to ride along cam slots 112 and 122 of jaw members 110 and 120, respectively. As jaw members 110 and 120 move distally, jaw members 110 and 120 will flex radially outwardly about hinge 116, away from each other and the longitudinal axis "X" (FIG. 6B). When spacer 150' is again in its initial distal most position, jaw members 110 and 120 will return to their initial open configuration and again be disposed at an angle θ relative to the longitudinal axis "X" (FIG. 6A).

Figure 7:
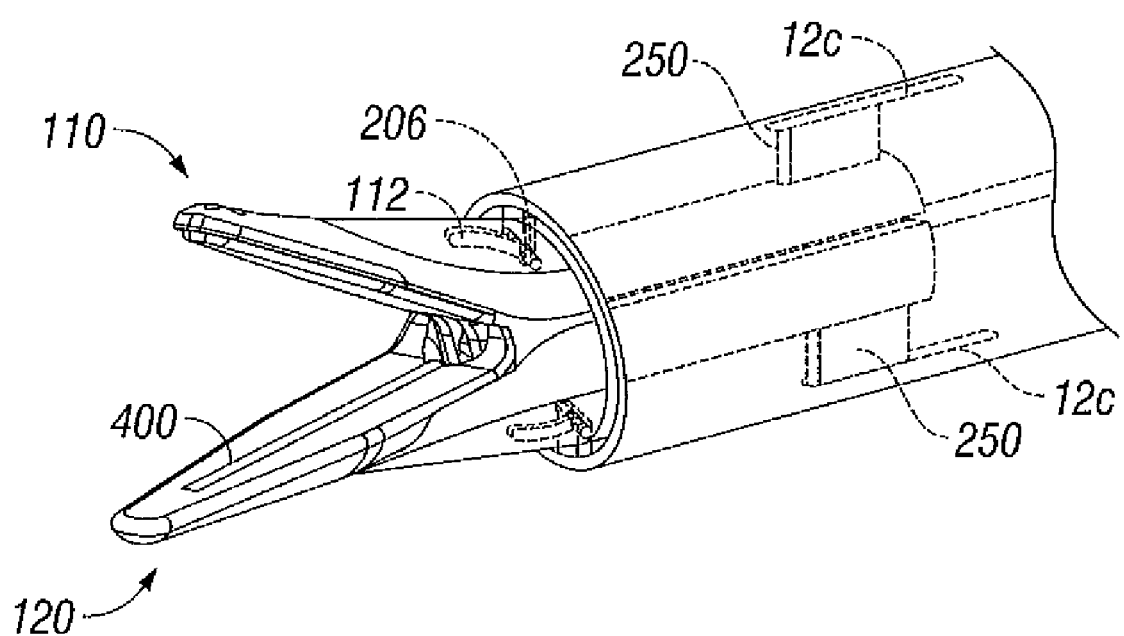
FIG. 7 is perspective view of an end effector assembly according to another embodiment in accordance with the present disclosure.
Figure 8A:
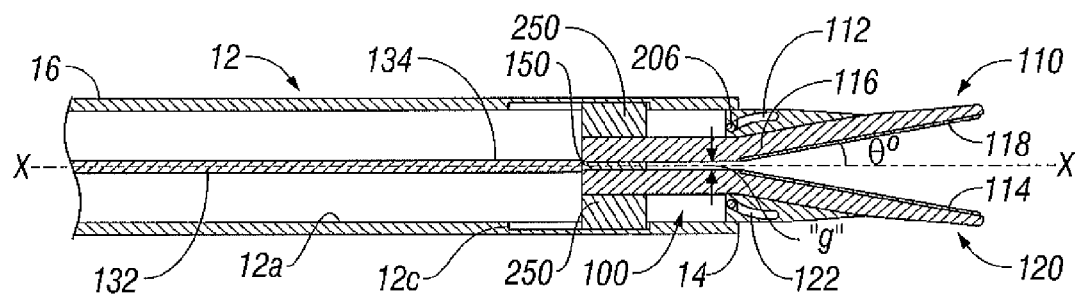
FIGS. 8A-8C illustrates the end effector assembly depicted in FIG. 7 in open, intermediate and closed configurations.
Figure 8B:
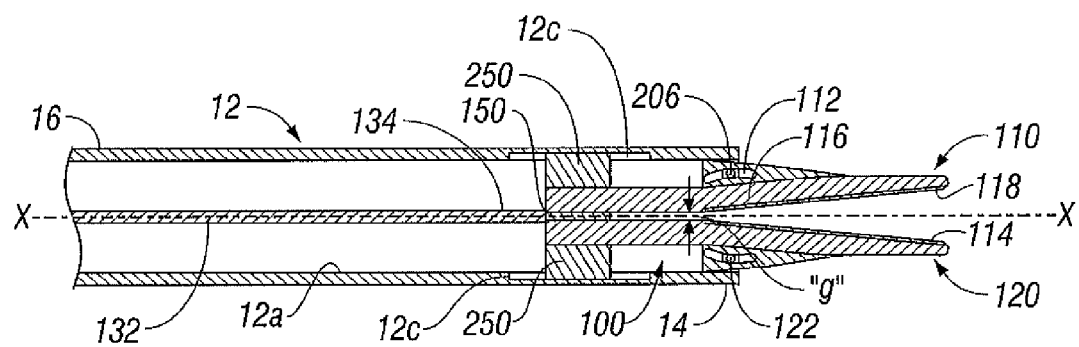
Figure 8C:
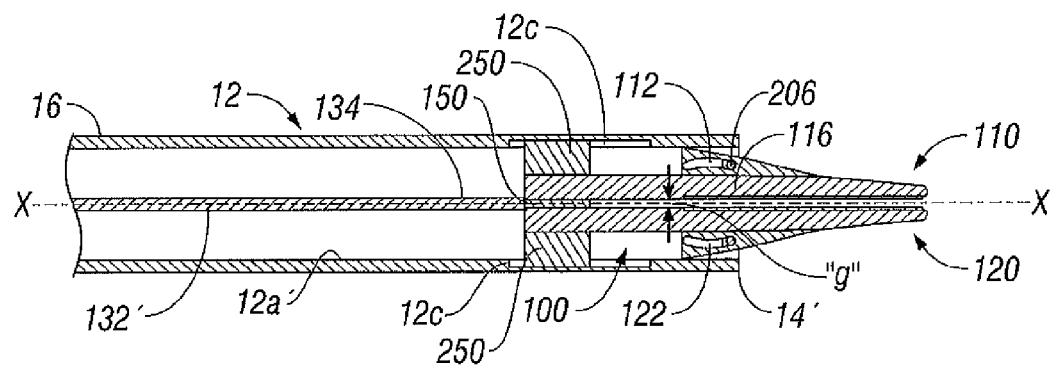

From the foregoing and with reference to the various figure drawings, those skilled in the art will appreciate that certain modifications can also be made to the present disclosure without departing from the scope of the same. For example, one or more grooves 12c (FIG. 7) may be operatively connected to one or more supports 250 (dual supports are shown operatively connected to groove 12c) at a distal 14 on inner surface 12a within shaft 12, Support 250, or portion thereof, is in operative communication with groove 12c and movable therein. A proximal end of support 250 is operatively connected to distal end of drive rod 132. Support 250 may be employed with and operatively connected to actuation tube 200 or jaw members 110 and 120. For illustrative purposes support 250 is shown operatively connected to both the jaw members.

Support 250 is operatively connected to jaw members 110 and 120 in such a manner that during proximal and distal translation of the support 250 each of the jaw members 110 and 120 will flex about living hinge 116. That is, as support 250 is moved in a proximal direction, jaw members 110 and 120, will translate proximally and flex radially inwardly, about living hinge 116, and as support 250 is moved in a distal direction, jaw members 110 and 120 will translate distally and flex radially outwardly, about living hinge 116.

While it is shown that support 250 is in operative communication with one or more grooves 12c and operatively connected to distal end of drive rod 132, such that jaw members 110 and 120 and support 250 move in unison, other mechanical configurations area contemplated. For example, support 250 may be rigidly affixed to inner surface 12a (i.e. support 250 remains stationary), and jaw members 110 and 120, or portions thereof, may be operatively connected to drive rod 132, such that proximal and distal translation of drive rod 132 causes jaw members 110 and 120 to move about support 250.

It is envisioned that inner surface 12a of shaft 12 or actuation tube 200 may both include one or more resilient members configured to bias cam pins 206 in a generally radially inwardly direction.

As mentioned above, a knife blade assembly may be configured to cut tissue and operably associated with the drive assembly. In this configuration jaw members 110 and 120 of end effector assembly 100 may each include a slot 400 for configured for receiving the knife blade, or portion thereof.

Figure 9:
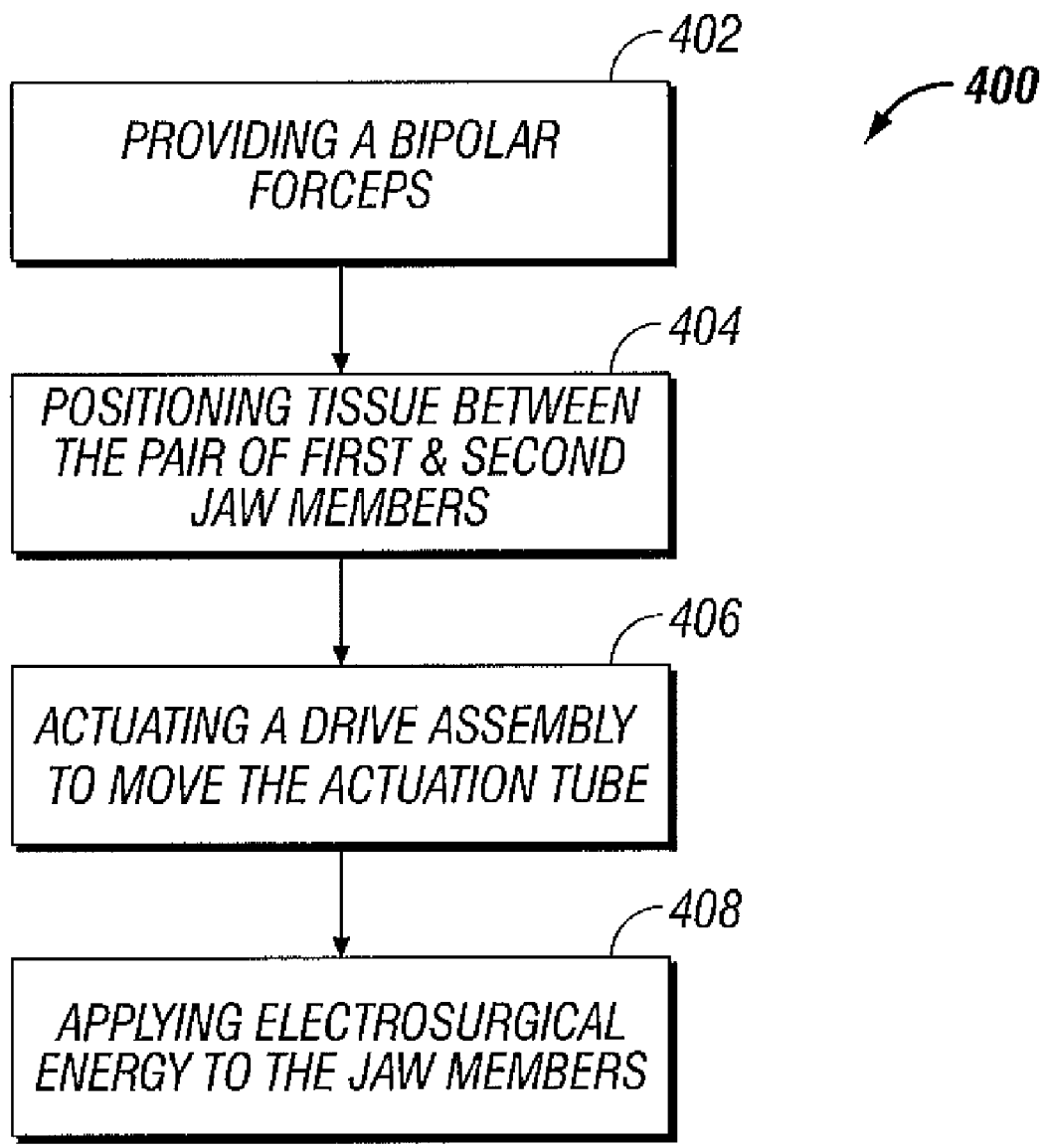
FIG. 9 is a flowchart illustrating a method for performing an electrosurgical procedure in accordance with the present disclosure.

The present disclosure also provides a method 400 for performing an electrosurgical procedure. As illustrated in FIG. 9, at step 402 a bipolar forceps is provided. The bipolar forceps includes a housing. The housing having a shaft that extends therefrom that defines a longitudinal axis therethrough. Disposed within he housing is a drive assembly being operable to reciprocate an actuation tube within the shaft to actuate a pair of first and second jaw members about a living hinge. Each of the jaw members includes a cam slot defined at a proximal end thereof. One or more of the jaw members is operatively connected to a distal end the actuation tube via a cam pin. At step 404 tissue is positioned between the pair of first and second jaw members such that a tissue seal may be effected. At step 406 the drive assembly is actuated to move the actuation tube causing the cam pin to cam the first and second jaw members to pivot about the living hinge and cam towards each other such that tissue is grasped therebetween. And at step 408 electrosurgical energy is applied to the jaw members such that a tissue seal may be effected therebetween.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. A bipolar forceps, comprising:
a housing having a shaft that extends therefrom that defines a longitudinal axis therethrough, the housing including a drive assembly disposed therein, the drive assembly being operable to reciprocate an actuation tube within the shaft, the actuation tube including a generally cylindrical configuration having a pair of cam pins extending laterally across an inside surface thereof; and
an end effector assembly operatively connected to a distal end of the shaft having a pair of first and second jaw members having outwardly facing surfaces and seal plates biased in an open configuration, each of the first and second jaw members being pivotable about a living hinge, each of the jaw members including a cam slot defined at a proximal end thereof, the cam slots positioned radially distal from the outwardly facing surfaces of each of the first and second jaw members such that from a closed to open configuration the first and second jaw members move towards each respective cam slot;
wherein at least one of the jaw members is operatively connected to a distal end of the actuation tube via at least one cam pin such that proximal reciprocation of the actuation tube cams each of the jaw members towards one another about the living hinge.

2. The bipolar forceps according to claim 1, wherein the jaw members are electrically isolated from each other via a non-conductive spacer disposed at a proximal end therebetween.

3. The bipolar forceps according to claim 2, wherein the spacer provides a gap distance from about 0.001 inches to about 0.006 inches between jaw members when closed.

4. The bipolar forceps according to claim 2, wherein the spacer provides a gap distance that is greater than 0.006 inches between jaw members when closed.

5. The bipolar forceps according to claim 1, wherein the cam slot of at least one jaw member is overmolded on the at least one jaw member.

6. The bipolar forceps according to claim 1, wherein at least one of the cam slots of one of the jaw members is arcuate.

7. The bipolar forceps according to claim 1, wherein the drive assembly includes an actuation rod coupled to the actuation tube to actuate the jaw members.

8. The bipolar forceps according to claim 1, wherein each jaw member includes an outer insulative housing that is overmolded to capture a sealing plate for engaging tissue, the outer insulative housing configured to include the cam slot at a proximal end thereof.

9. The bipolar forceps according to claim 1, wherein each jaw member includes an outer insulative housing and a sealing plate that are integrally formed together for engaging tissue, the outer insulative housing configured to include the cam slot at a proximal end thereof.

10. A bipolar forceps, comprising:
a housing having a shaft that extends therefrom which defines a longitudinal axis therethrough, the shaft including cam pins located at a distal end thereof and at least one groove, the housing including a drive assembly disposed therein, the drive assembly operable to reciprocate an actuation rod within the shaft; and an end effector assembly operatively connected to a distal end of the shaft having a pair of first and second jaw members having outwardly facing surfaces and seal plates, each of the first and second jaw members being pivotable about a living hinge, each of the jaw members including a cam slot defined at a proximal end thereof, the cam slots positioned radially distal from the outwardly facing surfaces of each of the first and second jaw members such that from a closed to open configuration the first and second jaw members move towards each respective cam slot and at least one support member operatively connected to the at least one groove;

wherein at least one of the jaw members is operatively connected to a distal end the actuation rod such that distal reciprocation of the actuation rod cams each of the jaw members towards one another about the living hinge.

11. The bipolar forceps according to claim 10, wherein the jaw members are electrically isolated from each other via a non-conductive spacer disposed at a proximal end therebetween.

12. The bipolar forceps according to claim 11, wherein the spacer provides a gap distance from about 0.001 inches to about 0.006 inches between jaw members when closed.

13. The bipolar forceps according to claim 11, wherein the spacer provides a gap distance that is greater than 0.006 inches between jaw members when closed.

14. The bipolar forceps according to claim 10, wherein the cam slot of at least one jaw member is over molded on the at least jaw member.

15. The bipolar forceps according to claim 10, wherein at least one of the cam slots of one of the jaw members is arcuate.

16. The bipolar forceps according to claim 10, wherein the drive assembly includes an actuation rod coupled to the actuation tube to actuate the jaw members.

17. The bipolar forceps according to claim 10, wherein each jaw member includes an outer insulative housing which is overmolded to capture a sealing plate for engaging tissue, the outer insulative housing being configured to include the cam slot at a proximal end thereof.

18. The bipolar forceps according to claim 10, wherein each jaw member includes an outer insulative housing and a sealing plate that are integrally formed together for engaging tissue, the outer insulative housing configured to include the cam slot at a proximal end thereof.

* * * * *